United States Patent [19]

Prine

[11] 4,402,756

[45] Sep. 6, 1983

[54] GRANULAR-FILLER MATERIAL AND ITS METHOD OF PREPARATION FROM PHOSPHATIC CLAYS

[75] Inventor: Robert G. Prine, Bartow, Fla.

[73] Assignee: Chesley B. Maddox, Lakeland, Fla. ; a part interest

[21] Appl. No.: 308,808

[22] Filed: Oct. 5, 1981

[51] Int. Cl.$^3$ .......................... C09C 1/02; C09C 1/42; C09C 3/00

[52] U.S. Cl. .................................. 106/288 B; 34/42; 37/195; 71/44; 71/47; 106/306; 252/435; 252/437; 299/10; 501/142; 501/155

[58] Field of Search ............................ 106/288 B, 306; 501/155, 142; 34/42; 37/195; 299/10

[56] References Cited

U.S. PATENT DOCUMENTS 2,571,866  10/1951  Greene ........................... 423/167 X
4,254,565  3/1981  Jenkins et al. ..................... 34/42 X

OTHER PUBLICATIONS

Tyler, P. M. et al., "Phosphatic Slime–A Potential Mineral Asset", Ind and Eng. Chem., 46(5), pp. 1049–1056.

*Primary Examiner*—Helen M. McCarthy
*Attorney, Agent, or Firm*—Duckworth, Allen, Dyer & Pettis

[57] ABSTRACT

A granular fertilizer and insecticide carrier-filler material which is produced from phosphatic clays is disclosed along with its method of production. The granular carrier-filler material is water-degradable, and is prepared from waste phosphatic clays by tilling the source material, allowing it to dry, crushing the dried material into granules, heating the granules at a temperature of about 450° F. to less than 1600° F. to obtain a granular carrier-filler material having a moisture content of no more than about 15% by weight. Depending upon end use applications, the granular carrier-filler material may be sized as by screening.

4 Claims, No Drawings

GRANULAR-FILLER MATERIAL AND ITS METHOD OF PREPARATION FROM PHOSPHATIC CLAYS

BACKGROUND OF THE INVENTION

1. Field of the Invention

The present invention relates to water-degradable carrier-filler materials and more particularly to the production of such materials from phosphatic clays which are normally discarded as a waste material by phosphate mining operations. While the granular carrier-filler material is primarily useful as a component of granular fertilizers and insecticides, it also has utility as an absorbent material and as a base for manufactured cat litter.

2. Description of the Prior Art

The use of carrier-filler materials in granular fertilizers and insecticides is certainly well known in the prior art. For example, for many years materials such as sand, crushed stone, coal slag, gravel and rocks have been used as excipients in the manufacture of nonliquid granular fertilizers and insecticides. However, such prior art carrier-filler materials possess inherent undesirable characteristics. For example, most such materials are not water-degradable; they generally provide no additional mineral nutrients; and they generally do not function as soil conditioners. Nevertheless, in order to provide commercially feasible granular fertilizers and insecticides such excipients must be utilized for the purpose of adding weight and bulk to the various combinations of ingredients necessary to achieve the desired proportions of such ingredients in a fixed unit of measure.

Because of the source material utilized in practicing this invention, namely phosphatic clays, any discussion of pertinent prior art must also consider the phosphate industry as it is presently conducted for the production of fertilizers. Phosphate rock ore, called matrix, is mined to produce phosphate materials of suitable purity and form for use as fertilizers, human and animal food product supplements, and other general chemical applications. Referring specifically to the Bone Valley formation in central Florida, this is the most important source of phosphate in the United States. More than one hundred million tons of phosphate ore are being mined annually in that area. As is well known in the phosphate industry, approximately one-third (⅓) of the total matrix mined is discarded as undesirable waste phosphatic clays which consist primarily of finely divided clay particles suspended in water and possessing properties that prevent effective settling. The high volume and extremely slow settling of the phosphatic clays requires that large land areas be devoted to massive settling ponds or basins for extended periods without any further productive use. This relatively inefficient land use, coupled with the loss of water and phosphate values contained in the suspended phosphatic clays, provides a high degree of motivation within both the government and the phosphate industry to develop a practical, cost-effective solution to the problem of phosphatic clay disposal.

Thusfar numerous individuals and organizations, including the U.S. Bureau of Mines, have studied the problem and failed to develop a practical, cost-effective solution. For example, U.S. Pat. No. 2,569,323 to Maynard discloses a method of applying a process known as "bloating" to produce a lightweight aggregate suitable for construction purposes from phosphate wastes, commonly referred to as phosphate slime. Thus, the Maynard patent does teach an invention for utilizing the phosphate waste material in a productive manner. However, his method calls for extruding consolidated slimes and then firing the extrusion at temperatures of at least 1600° F. to cause bloating thereof. The result of the Maynard process is the production of a hard, durable lightweight aggregate. The result of the Maynard process certainly would not be suitable as a carrier-filler material such as that of this invention for the reason that it is not water-degradable, it would not provide a secondary source of mineral nutrients, and it would not function as a soil conditioner. Furthermore, since this patent issued to Maynard in 1951, the cost of energy has increased dramatically. It seems clear that the cost of producing temperatures in excess of 1600° F. would severely militate against the commercial feasibility of his method.

Other prior art patents have recognized the feasibility of producing aggregate-type materials by heating clay or similar earthy material to both expand and dry the material. U.S. Pat. No. 2,015,381 to Harding, et al., teaches a method wherein the raw material is fused at a temperature materially above 2000° F. A similar bloated product is taught in U.S. Pat. No. 2,478,757 to Foster. This patent teaches the desirability of heating at temperatures of the order of 1600° F. to 2200° F. Similar pertinent, though clearly distinct from the present invention, teachings are presented in U.S. Pat. Nos. 1,920,773 to Walton and 1,751,163 to Loessin.

Insofar as prior art means for efficiently treating phosphatic clay wastes is concerned, Information Circular 8668 titled "The Florida Phosphate Slimes Problem" published in 1975 by U.S. Bureau of Mines, is a most thorough review and bibliography. As stated in that publication, no completely satisfactory solution has been developed. Of particular note is the fact that in the portion of the pamphlet concerning recommendations for future research, there is virtually no suggestion of any means for efficiently and economically recovering the phosphate material from the clays so that it may be put to use.

It is therefore apparent that there is a great need in the art not only for means of dealing with the efficient disposal of phosphatic clays, but also of providing an economical, water-degradable carrier-filler material useful in the fertilizer industry and possessing qualities of providing a secondary source of mineral nutrients and functioning as a soil conditioner.

SUMMARY OF THE INVENTION

Broadly stated, the present invention comprises a water-degradable granular carrier-filler material suitable for use in either fertilizer or insecticide compositions. In addition, the carrier-filler material may be utilized as an absorbent material for retaining and holding oil as in automotive repair shops, or as a base for manufactured litter material. The invention further comprises a unique method for preparing the carrier-filler material from phosphatic clays.

As broadly indicated above, waste phosphatic clays, generically referred to as slimes, are a byproduct of the phosphate industry. Current industry standards involve placing the slimes in settling ponds or basins where they are allowed to settle, dry and agglomerate naturally to a physical state or condition where the slime can be excavated and the land reclaimed. The method of the present invention begins with the selection of a settling pond which has been out of use long enough for the clays to have settled and dried naturally to a point where they will support the weight of mining machinery and can be excavated in the form of clods or lumps. Such settling ponds are generally covered with marsh-type trees, bushes and grasses which should be removed before attempting to excavate the naturally dried clays.

After a suitable phosphatic clay settling pond has been selected and the surface thereof cleared of vegetation by any convenient means, the surface of the deposit is tilled as by a disk harrow or a rotary cultivator to break the clay into clods. If convenient, the tilled material is left in place until such time as further natural drying action occurs. On the other hand, the tilled material may be excavated and transported to a more suitable place for such natural drying to occur. Both towed and motorized scrapers and tractor shovels have all proved to be satisfactory means for excavating and transporting the tilled material. It is, of course, obvious that these natural drying actions may be accomplished in a more timely and cost-effect manner during periods of substantially hot, dry weather.

Once the tilled clays have been allowed to dry naturally to a non-agglomerating physical state, the material is then fed by known means into a delumper-crusher to reduce the size of the clods further without unduly pulverizing them. A crusher of the low-speed impact breaker type has proved to be a satisfactory machine for that purpose.

Once the material has passed through the crusher it is then fed by suitable conveying means into a furnace for the application of sufficient heat to dehydrate the material further to a free moisture content of between 0 and 15%, by weight. At this point it should be noted that throughout the description and claims of this invention all reference to moisture content is made with regard to free moisture, only. It is definitely preferred that the furnace be of a nonpulverizing type, and for reasons of economy gas or oil firing is preferred to the utlization of electrical energy. It has been determined that a gas-fired, screw-type dryer gives satisfactory results with minimal generation of flue dust or additional pulverization. The time required to complete the drying process depends upon the free moisture content of the feed material and the temperature of the furnace. Furnace temperatures ranging from 400° F. to 1000° F. provide satisfactory results, but temperatures of 1600° F. and higher must be avoided in order to preclude bloating of the material, thereby rendering it unsuitable for its intended uses. Care must also be taken during the drying process to avoid reducing the moisture content of the material beyond the elimination of free water, as opposed to water of hydration. Should this happen, the material will tend to lose its granular form during subsequent processing, handling and use. That is to say, the granular nature of the desired final product will be lost, and the undesirable result will be a fine powder.

From the above it is to be appreciated that drying time is determined with regard to the initial moisture content of the feed material primarily by varying the speed at which the feed material passes through the furnace and the temperature to which the material is exposed. Again it is emphasized that temperatures above 1600° F. are to be avoided and that temperatures of from 450° F. to 1000° F. are preferred.

The dried granules from the furnace may then be placed by any convenient means such as, for example, a belt conveyor, onto means for sizing the granular carrier-filler material to obtain granules of predetermined sizes for the various end use applications. A multiple-deck vibrating screen is quite satisfactory as a sizing means. More specifically, a double-deck vibrating screen equipped with a six mesh top screen and a sixteen mesh bottom screen has produced satisfactory results. Oversize material may be recirculated through the method described above to achieve further size reduction. Undersize material may be reagglomerated by wetting and then reprocessed. Obviously, additional screening decks and various screen sizes may be used for the purpose of obtaining a variety of granular material sizes.

The resulting water-degradable granular material is quite suitable for use as a filler in dry fertilizer mixtures. It may also be used as a carrier for insecticide, with or without the addition of fertilizers. Accordingly, the principal object of the present invention is to provide a novel granular fertilizer and insecticide carrier-filler material and its method of production from waste phosphatic clays. A further object of the present invention is to provide a novel method of producing a granular material from waste phosphatic clays which is suitable for use as an absorbent material. Still another object of the present invention is to provide a novel method of producing a granular material from waste phosphatic clays which is suitable for use as a base material in the manufacture of cat litter. Yet another object of the present invention is to provide an economical, nonhazardous use for waste phosphatic clays.

The invention accordingly comprises the several steps and the relation of one or more such steps with respect to each of the others, and the product possessing the features, properties, and the relation of components which are exemplified in the following detailed description, and the scope of the invention will be indicated in the claims.

DETAILED DESCRIPTION

The present invention relates to a water-degradable granular carrier-filler material and its method of production from phosphatic clays. The following detailed description is given, then, in order to describe fully the granular carrier-filler material and its preferred method of preparation. However, before proceeding to the presentation of a detailed description of the preferred method and the resulting product, further attention should be given to the present state of the art in the phosphate industry for more complete appreciation of the value of the method and resulting material of this invention.

Literally all mining of phosphate rock in the Bone Valley Formation of central Florida is accomplished by open pit methods. Once the overburden has been removed and the phosphate-rich rock has been mined, chemical processes are utilized for converting the rock to fertilizer. The production of fertilizer from the phosphate-rich rock accounts for about 98% of Florida's rock production. After mining an initial step in the process for converting the ore to fertilizer material is termed "beneficiation." Generally stated, beneficiation may be defined as a washing process for obtaining ore of suitable quality for further processing. As a result of the beneficiation program, literally huge amounts of phosphatic clay, or "slimes," waste materials are generated. These phosphatic clays constitute approximately one-third ($\frac{1}{3}$) of the total ore mined and are primarily a suspension of clay particles in water. The particles are extremely finely divided and have properties that prevent effective settling. It should also be noted that relatively large amounts of phosphate materials are lost to any further use as part of the phosphatic clay suspension.

These phosphatic clay suspensions are currently stored in large, above ground settling ponds where, after a number of years, natural drying and substantial solidification takes place. While the phosphate industry has been and continues to be involved in active research to determine means for hastening the settling process, it is to be remembered that the scope of the present invention concerns use of naturally dried phosphatic clays and not dewatering, per se.

Of particular significance in the present invention as regards the use of granulated phosphatic clays in non-liquid fertilizer and insecticide mixtures is the fact that the phosphatic clays contain valuable quantities of tricalcium phosphate a mineral nutrient, as well as calcium oxide (CaO), magnesium oxide (MgO) and clays which do function as soil conditioners. The following table reflects the theoretical mineralogical composition of Florida phosphatic clays.

| Mineralogical Composition of Florida Phosphatic Clays | | |
|---|---|---|
| Mineral | Wt-Pct | Theoretical Composition |
| Carbonate-fluorapatite | 20–25 | $Ca_{10}(PO_4,CO_3)_6F_{2-3}$ |
| Quartz | 30–35 | $SiO_2$ |
| Montmorillonite | 20–25 | $(Fe,Al,Mg)_2(Al,Si)_4O_{10}(OH)_2(Ca,Na)$ |
| Attapulgite | 5–10 | $(Mg,Al,Fe)_5(Al,Si)_6O_{20}(OH)_2 8H_2O$ |
| Wavellite | 4–6 | $Al_3(OH)_3(PO_4)_2 5H_2O$ |
| Feldspar | 2–3 | $KAlSi_3O_8 + NaAlSi_3O_8$ |
| Heavy Minerals | 2–3 | Zircon, garnet, ilmenite, rutile |
| Dolomite | 1–2 | $CaMg(CO_3)_2$ |
| Miscellaneous | 0–1 | Kaolinite, crandallite, hydrated feric oxide, organic |

Chemical analysis of Florida phosphatic clays reveals the following typical composition.

| Typical Chemical Composition of Florida Phosphatic Clays | | |
|---|---|---|
| | Analysis, Percent | |
| Constituent | Typical | Range |
| $P_2O_5$ | 9.1 | 9–17 |
| $SiO_2$ | 45.7 | 31–46 |
| $Fe_2O_3$ | 4.0 | 3–7 |
| $Al_2O_3$ | 8.5 | 6–18 |
| CaO | 13.9 | 14–23 |
| MgO | 1.1 | 1–2 |
| CO | .8 | Trace–1 |
| Fluorine | .9 | Trace–1 |
| Loss on ignition at 1,000C | 10.6 | 9–16 |
| BPL(Bone phosphate of lime or $Ca_3P_2O_8$) | 19.9 | 19–37 |

Referring specifically to the above phosphatic clays, the first step in the method of the present invention is selection of a settling pond which has been out of use long enough for the clays to have settled and dried naturally to a point where they will support the weight of mining equipment and can be excavated in the form of clods or lumps. After a suitable pond has been selected and the surface cleared of vegetation the clay deposit is tilled as by a disk harrow to loosen and break the material into clods. Considering general weather conditions in central Florida, the tilled material may be left in place for further natural drying. If desired, the tilled clods may be transported to a more suitable location for additional natural drying to occur.

These clods are allowed to dry naturally until they have obtained a non-agglomerating physical state. Next, the dried clods are passed by conventional means through a low speed impact-type crusher to reduce their size further without unduly pulverizing them. Granules of phosphatic clays are obtained from the output of the crusher.

These granules are next fed by conventional means into a heating means wherein the free moisture content is reduced to a range of from 0 to 15%, by weight. The heating means is preferably gas or oil fired and of a non-pulverizing type. A gas-fired, screw-type dryer is preferred for the reason that it adequately and efficiently dehydrates the granules with minimal generation of flue dust and no additional pulverization of the granules. The temperature of the furnace is maintained in the range of 450° F. to less than 1600° F. and is preferably no more than about 1,000° F. Obviously, the time required to complete the drying process is dependent upon the free moisture content of the feed granules, the speed at which the granules move through the furnace, and the temperature thereof. It is important to note that temperatures of about 1600° F. and higher must be avoided to preclude bloating the granules and rendering them unsuitable for use as a water-degradable carrier-filler material. Care must also be taken during the drying process to avoid removing water other than free moisture content. Otherwise, the material will tend to lose its granular form during subsequent handling and use.

The dried granules may then be transported by standard means to a sizing station. A double-deck vibrating screen equipped with a six mesh top screen and a sixteen mesh bottom screen has been utilized with satisfactory results. Oversize material may be recycled to achieve further size reduction as might be necessary. Undersize material may be reagglomerated by wetting and then reprocessed.

The resultant water-degradable carrier-filler material may be advantageously utilized as an excipient in dry fertilizer and insecticide preparations. With reference to the above tables, it can be seen that the product of this invention does contain significant quantities of mineral nutrients in the form of bone phosphate of lime or tricalcium phosphate. Soil conditioners in the form of calcium oxide and magnesium oxide are also present. Furthermore, unlike prior art uses and processes for phosphate slimes, the product of this invention is water-degradable, significantly increasing its utility in industry. Furthermore, primarily because of the clay constituents in the product, the carrier-filler material of this invention may also be successfully utilized as an absorbent for both organic and aqueous liquids.

Modifications, alterations and deviations from the specific materials and method steps described above will obviously occur to those skilled in the art without departing from the spirit or scope of the invention as set forth in the claims. However, it is important in the practice of this invention to avoid undue pulverization of the phosphatic clays and to avoid the use of excessively high drying temperatures.

It will thus be seen that the objects set forth above, among those made apparent from the preceding description, are efficiently attained, and since certain changes may be made in carrying out the above method and in the product set forth without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. A method for obtaining a granular carrier-filler material from phosphatic clays wherein said material is water-degradable and is suitable for use as a fertilizer carrier-filler, an insecticide carrier-filler, an oil absorbent, and a litter base, said method comprising the steps of:
   a. selecting a source of phosphatic clays which has settled and dried naturally to a physical state capable of supporting the weight of mining machinery, said clays consisting essentially of 9–17% $P_2O_5$; 31–46% $SiO_2$; 3–7% $Fe_2O_3$; 6–18% $Al_2O_3$; 14–23% CaO; 1–2% MgO; trace–1% CO; trace–1% Fluorine; 9–16% loss on ignition at 1,000° C.; 19–37% BPL;
   b. tilling said source to obtain clods;
   c. drying said clods to a non-agglomerating physical state;
   d. crushing said dried clods to obtain granules;
   e. heating said granules at a temperature of about 450° F. to about 1,000° F. to remove mechanically bound water only to obtain said granular-filler material having a moisture content of no more than about 15%, by weight.

2. The method of claim 1 wherein said drying is accomplished naturally.

3. The method of claim 1 further comprising the step of sizing said granular carrier-filler material to obtain dehydrated granules of predetermined sizes for end use.

4. A water-degradable granular-filler material of the type primarily intended for use as a filler and absorbent material obtained according to the method of claim 1.

* * * * *